United States Patent [19]
Koyama et al.

[11] Patent Number: 4,824,938
[45] Date of Patent: Apr. 25, 1989

[54] WATER-SOLUBLE DRY SOLID CONTAINING PROTEINACEOUS BIOACTIVE SUBSTANCE

[75] Inventors: Shunsaku Koyama; Toshio Miyake, both of Okayama, Japan

[73] Assignee: Kabushiki Kaisha Hayashibara Seibutsu Kagaku Kenkyujo, Okayama, Japan

[21] Appl. No.: 93,089

[22] Filed: Aug. 31, 1987

Related U.S. Application Data

[63] Continuation of Ser. No. 729,191, May 1, 1985, abandoned.

[30] Foreign Application Priority Data

Jun. 6, 1984 [JP] Japan ................................ 59-116158

[51] Int. Cl.$^4$ ...................... C07K 15/00; A61K 37/02; A61K 37/24; A61K 37/48
[52] U.S. Cl. ..................................... 530/351; 530/350; 530/399; 424/85.1; 424/94.1; 424/94.2; 424/94.3; 514/2; 514/3; 514/8; 514/23; 435/102; 435/188; 536/1.1
[58] Field of Search ...................... 530/350, 351, 399; 424/85; 514/2, 3, 8, 23; 435/102, 188; 536/1.1

[56] References Cited

U.S. PATENT DOCUMENTS

| 4,247,642 | 1/1981 | Hirohara et al. | 435/181 |
| 4,372,883 | 2/1983 | Matuhashi et al. | 530/83 F |
| 4,474,756 | 10/1984 | Mitsuhashi et al. | 424/88 |
| 4,536,387 | 8/1985 | Sakamoto et al. | 424/28 |

FOREIGN PATENT DOCUMENTS 2001955  5/1981  United Kingdom .
2096146 10/1982  United Kingdom .
2095552 10/1982  United Kingdom .

OTHER PUBLICATIONS

Mitsuhashi et al., CA, vol. 97, 1982, #188261r.
Matsuhashi et al., CA, vol. 95, 1981, #17578y.

Primary Examiner—Howard E. Schain
Assistant Examiner—Garnette D. Draper
Attorney, Agent, or Firm—Browdy and Neimark

[57] ABSTRACT

Proteinaceous bioactive substances (including lymphokine and peptide hormone) in dry solid are extremely stabilized by the presence of the specific polysaccharide mainly composed of repeating maltotriose units. Pullulan, elsinan, and their partial hydrolysates are feasible as the polysaccharide. The weight ratio of the polysaccharide to the substance which effectively stabilizes the latter substance is at least 0.5 on the basis of dry solids. The dry solid is advantageously usable as a test reagent, injection, granule, tablet, suppository or ointment.

11 Claims, No Drawings

WATER-SOLUBLE DRY SOLID CONTAINING PROTEINACEOUS BIOACTIVE SUBSTANCE

This application is a continuation of application Ser. No. 729,191 filed May 1, 1985 now abandoned.

FIELD OF THE INVENTION

The present invention relates to a stabilized water-soluble dry solid containing a proteinaceous bioactive substance along with a polysaccharide mainly composed of repeating maltotriose units.

ABBREVIATIONS

Interferon is abbreviated herein as "IFN"; human interferon, "HuIFN"; tumor necrosis factor, "TNF"; lymphotoxin, "LT"; growth hormone, "GH"; erythropoietin, "EPO"; epidermal growth factor, "EGF"; and thyroid-stimulating hormone, "TSH".

The "h" prefixed to some of these abbreviations means that the specific substance is human-specific (i.e. hGH, hEGF, hEPO, and hTSH).

BACKGROUND OF THE INVENTION

Proteinaceous bioactive substances usable as test reagent and/or pharmaceutical, e.g. lymphokines and peptide hormones, have been extensively studied and developed as the recent remarkable advances in biochemistry and medical science. Some of these substances are commercialized or readily for commercialization.

Since proteinaceous bioactive substances are, in general, relatively unstable, a stabilizer must be added for their commercialization. The stabilizer most frequently used is human serum albumin (HSA). The use of HSA is, however, disadvantageous because:

(1) The stabilization effect on proteinaceous bioactive substances is unsatisfactory;

(2) The addition of HSA obscures the specific activity of the substance. A specific activty is represented by activity/mg protein, and used for determination of purification degree;

(3) The use of HSA has a fear of mediating human infectious diseases since HSA is a protein derived from human serum;

(4) HSA tends to form a water-insoluble solid on drying.

In order to avoid these demerits of HSA, various stabilizers have been proposed. As a stabilizer for IFN, Japan Patent Kokai No. 92,691/83 proposes cyclodextrin, and Japan Patent Kokai No. 25,333/84 proposes saccharides (excluding polysaccharides) such as mono- and oligo-saccharides, and polyols such as glycerine and ethylene glycol. For TNF stabilization, Japan Patent Kokai No. 39,829/84 proposes non-ionic surface active agents, and Japan Patent Kokai No. 59,625/84 proposes D-glucose, D-galactose, D-xylose, D-glucuronic acid, dextran, hydoxyethyl starch, and, preferably, trehalose. The stabilization effects attained with these stabilizers have proved insufficient. In addition, trehalose is relatively expensive. Thus, these stabilizers have not been in practical use.

DETAILED DESCRIPTION OF THE PREFERRED EMBODIMENT

We investigated various stabilizers, especially polysaccharides, to obtain a highly-stable water-soluble dry solid containing a proteinaceous bioactive substance. As the result, we found that a polysaccharide, mainly composed of repeating maltotriose units, unexpectedly satisfies the objects of the present invention. More particularly, we found that a dry solid obtained by drying an aqueous solution, containing the substance along with the specific polysaccharide, by evaporation has a desirable water-solubility, as well as that the dry solid much more stably retains the activity of the substance. This is the present invention.

The term "proteinaceous bioactive substance" as used herein means proteinaceous substances which exhibit a bioactivity in vivo, such as simple proteins and protein conjugates, in particular, lymphokines, such as IFN, LT, TNF, macrophage migration inhibitory factor, transfer factor, T cell growth factor, and colony stimulating factor; and peptide hormones, such as insulin, GH, prolactin, chorionic gonadotropin, EPO, follicle-stimulating hormone, luteinizing hormone, EGF, adrenocorticotropic hormone, placental lactogen, TSH, and parathyroid hormone, which have a molecular weight within the range from about 10,000 daltons to about 200,000 daltons.

The proteinaceous bioactive substances usable in the invention include those which may be isolated from body fluid, cell, tissue or organ wherein such substance naturally occurs; those which may be recovered from an in vitro or in vivo culture of any of the above; those which may be recovered from a culture of either human cell, animal cell or microorganism wherein the producibility of such substance is engineered by conventional means, e.g. cell fusion, gean recombinant technique, etc.; but are not restricted to those which may be prepared by particular procedures.

The polysaccharides usable in the invention are those which are mainly composed of maltotriose units polymerized in α-fashion. Examples of the polysaccharides are pullulan, elsinan, and their partial hydrolysates having a molecular weight within the range of 10,000–10,000,000 daltons, preferably within then range of 20,000–2,000,000 daltons. The weight ratio of the polysaccharide to the substance is at least 0.5, desirably, from 1.0 to 10,000, on the basis of dry solids.

The aqueous solution containing a proteinaceous bioactive substance along with the polysaccharide is dried under conditions appropriate to give a water-soluble dry solid without substantial decrease in the activity of the substance. Although conventional drying procedures carried out at a reduced pressure and a temperature below 30° C. are feasible in the invention, freeze-drying is desirable. In addition to the specific polysaccharide, one or more additional substances, e.g. mineral, buffer, amino acid, saccharide, etc., may be desirably incorporated into the aqueous solution, prior to its drying. The dry solid thus obtained is readily dissolvable in water, and very stably retains the activity of a proteinaceous bioactive substance. Thus, the dry solid is advantageously usable for, e.g. test reagent, injection, medicine for external or internal administration, etc., to prevent and/or treat human diseases.

The following experiments will further explain the present invention.

EXPERIMENT 1

Stabilization test on IFN

EXPERIMENT 1-A

Preparation of IFN

Newborn hamsters were injected with an antiserum, prepared with rabbit in conventional manner, to weaken their immunoreaction, subcutaneously implanted with BALL-1 cell, and fed for three weeks in usual way. The tumor masses, formed subcutaneously in the animals, were extracted, minced, and disaggregated in saline. The cell so obtained was washed with serum-free RPMI 1640 medium (pH 7.2), suspended in a fresh preparation of the same culture medium to give a cell density of about $2 \times 10^6$ cells/ml, and kept at 35° C. The cell suspension was added with a partially purified HuIFN in a dose of 200 U/ml, incubated for about two hours, added with Sendai virus (about 300 hemagglutination titers/ml), and incubated for additional twenty hours to induce HuIFN production. The resultant culture was centrifuged to about $1,000 \times g$ and about 4° C. to remove the solid, and the supernatant was membrane-filtered. The filtrate was chromatographed with a column of conventional immobilized anti-HuIFN antibody, and the non-adsorbed fractions were removed. The adsorbed HuIFN was eluted from the column, and concentrated with a membrane to obtain an about 0.01 w/v % concentrate with a specific activity of about $1.5 \times 10^8$ U/mg protein in a yield of about 4 ml/hamster.

The activity of HuIFN was assayed by the conventional plaque reduction method using FL cell. The hemagglutination titers were assayed in accordance with the method as described by J.E. Salk, *The Journal of Immunology*, Vol. 49, pp. 87-98 (1944).

EXPERIMENT 1-B

Comparison of stabilization effects of several stabilizers on IFN

One-half ml of an HuIFN concentrate, obtained by the method in Experiment 1-A, and 1 ml aqueous solution of a stabilizer were placed in a glass vial, admixed, freeze-dried, and stored at either 4° C. or 37° C. for two months. The solid was added with 30° C. saline to dissolve or elute HuIFN. The HuIFN was assayed, and the retension ratio (%) to the activity obtained before the freeze-drying was calculated with the following equation:

$$\text{Retension ratio (\%)} = \frac{\text{Activity on the storage}}{\text{Activity before the freeze-drying}} \times 100$$

The results are listed in Table I.

These results evidently confirmed that the dry solids using as the stabilizer the specific polysaccharide, i.e. pullulan or elsinan, were excellent in HuIFN stability and water-solubility, and, therefore, handleable with ease.

TABLE I

| Stabilizer | Solubility in saline | Retension ratio (%) 4° C. | Retension ratio (%) 37° C. | Remark |
|---|---|---|---|---|
| None | Readily soluble | 60.9 | 0 | Control |
| Phosphate buffer | Readily soluble | 68.3 | 15.2 | Control |
| Maltose | Readily soluble | 72.4 | 41.2 | Control |
| β-Cyclodextrin | Readily soluble | 78.1 | 45.6 | Control |
| HSA | Soluble | 86.2 | 67.3 | Control |
| Amylopectin | Soluble | 80.1 | 59.2 | Control |
| Hydroxyethyl starch | Readily soluble | 78.3 | 56.6 | Control |
| Dextran | Readily soluble | 81.5 | 65.3 | Control |
| Pullulan | Readily soluble | 100.0 | 100.0 | Present invention |
| Elsinan | Readily soluble | 100.0 | 99.1 | Present invention |
| Gum arabic | Readily soluble | 76.2 | 54.6 | Control |
| Gum tragacanth | Readily soluble | 77.3 | 52.1 | Control |
| Carrageenan | Readily soluble | 75.4 | 48.7 | Control |
| Agar | Scarcely soluble | 33.1 | 21.6 | Control |
| Pectin | Readily soluble | 50.3 | 25.3 | Control |

Note:
In the column of "stabilizer", "none", only deionized water; "phosphate buffer", 0.01 M phosphate buffer (pH 7.2); and the others, 0.5 w/v % aqueous solution of the specified stabilizer.

EXPERIMENT 2

Stabilization test on TNF

EXPERIMENT 2-A

Preparation of TNF

Newborn hamsters were injected with an antiserum, prepared with rabbit in conventional manner, to weaken their immunoreaction, subcutaneously implanted with an SV-40 virus-transformed human monocyte line, fed for one week in usual way, intraperitoneally injected with crude BCG cell in a dose of $10^7$ cells/hamster, and fed for an additional two weeks. The tumor masses, formed subcutaneously in the animals, about 15 g each, were extracted, minced, and disaggregated in saline containing trypsin. The cell so obtained was washed in Eagle's minimal essential medium (pH 7.2) supplemented with 5 v/v % human serum, suspended in a 37° C. fresh preparation of the same culture medium to give a cell density of about $5 \times 10^6$ cells/ml, added with *Escherichia coli* endotoxin (about 10 μg/ml), and incubated at this temperature for sixteen hours to induce TNF production.

The resultant culture was centrifuged at about $1,000 \times g$ and about 4° C. to remove the solid, after which the supernatant was dialyzed against saline containing 0.01 M phosphate buffer (pH 7.2) for twenty-one hours, and membrane-filtered. The filtrate was concentrated, and freeze-dried to obtain a powder with TNF activity. The powder was purified by adsorption/desorption using ion exchange, molecular weight fractionation using gel filtration, concentration, and membrane-filtration, in accordance with the procedures as reported in G. Bodo, *Symposium on Preparation, Standardization and Clinical Use of Interferon* (11-th International Immunological Symposium, 8 & 9 June 1977, Zagreb, Yugoslavia). The resultant HuIFN-free preparation was salted out with ammonium sulfate, purified by affinity-chromatography using Con A-Sepharose, and concentrated to obtain an about 0.01 w/v % concentrate containing a high-purity TNF in a yield of about 30 ml/hamster: TNF was characterized in that it effected hemorrhagic necrosis on Meth A sarcoma, but did not affect on normal cells. The TNF thus obtained was a glycoprotein with a specific activity of about $3.5 \times 10^5$ U/mg protein, and free of the inducer used.

The activity of TNF was assayed in conventional manner as reported in *Lymphokines*, Vol. 2, edited by E. Pick, pp. 235-272, "Tumor Necrosis Factor", published by Academic Press, Inc. (1981): After exposing a culture of L-929 cell (TNF-susceptive normal cell line) to dilutions of TNF for the prescribed time, the number of residual treated cells was counted.

EXPERIMENT 2-B

Comparison of stabilization effects of several stabilizers on TNF

Similarly as in Experiment 1-B, 0.5 ml of a TNF concentrate, obtained by the method in Experiment 2-A, and 1 ml aqueous solution of a stabilizer were placed in a glass vial, freeze-dried, and stored, followed by determination of the retention ratio (%).

The results are listed in Table II.

TABLE II

| Stabilizer | Solubility in saline | Retention ratio (%) 4° C. | Retention ratio (%) 37° C. | Remark |
|---|---|---|---|---|
| None | Readily soluble | 43.8 | 0 | Control |
| Phosphate buffer | Readily soluble | 46.2 | 6.7 | Control |
| Maltose | Readily soluble | 62.5 | 22.3 | Control |
| β-Cyclodextrin | Readily soluble | 60.3 | 25.7 | Control |
| HSA | Soluble | 76.1 | 40.9 | Control |
| Amylopectin | Soluble | 64.3 | 41.7 | Control |
| Hydroxyethyl starch | Readily soluble | 70.9 | 36.9 | Control |
| Dextran | Readily soluble | 78.2 | 43.6 | Control |
| Pullulan | Readily soluble | 100.0 | 99.4 | Present invention |
| Elsinan | Readily soluble | 100.0 | 98.2 | Present invention |
| Gum arabic | Readily soluble | 63.8 | 28.6 | Control |
| Gum tragacanth | Readily soluble | 70.4 | 30.1 | Control |
| Carrageenan | Readily soluble | 62.6 | 25.2 | Control |
| Agar | Scarcely soluble | 25.1 | 10.5 | Control |
| Pectin | Readily soluble | 28.8 | 16.3 | Control |

Note:
In the column of "stabilizer", "none", only deionized water; "phosphate buffer", 0.01 M phosphate buffer (pH 7.2); and the others, 0.5 w/v % aqueous solution of the specified stabilizer.

These results evidently confirmed that the dry solids using as the stabilizer the specific polysaccharide, i.e. pullulan or elsinan, were excellent in TNF stability and solubility in water, and, therefore, handleable with ease.

EXPERIMENT 3

Ratio of polysaccharide

The stabilization effect on proteinaceous bioactive substances was studied with different weight ratios of the polysaccharide: One-half ml of either an HuIFN concentrate, obtained by the method in Experiment 1-A, or a TNF concentrate, obtained by the method in Experiment 2-A, was placed in a glass vial along with either pullulan or elsinan having an appropriate concentration to give a weight ratio of the polysaccharide to the substance of either 0, 0.01, 0.1, 0.5, 1.0, 5.0, 10.0, or 100.0 on the basis of dry solids, mixed, freeze-dried similarly as in Experiment 1-B, and stored at 37° C. for one month, followed by determination of the retention ratios (%).

The results are listed in Table III.

All the dry solids were readily dissolvable in saline.

As is evident from these results, the weight ratio which effectively stabilizes a proteinaceous bioactive substance is 0.5 or higher, preferably, 1.0 or higher, on the basis of dry solids.

TABLE III

| Polysaccharide | Weight ratio to protein (folds) | Retension of HuIFN (%) | Retension of TNF (%) |
|---|---|---|---|
| Pullulan | 0 | 0 | 0 |
| | 0.01 | 12.3 | 0 |
| | 0.1 | 34.5 | 28.4 |
| | 0.5 | 87.2 | 83.5 |
| | 1.0 | 94.6 | 89.9 |
| | 5.0 | 98.3 | 96.2 |
| | 10.0 | 100.0 | 97.8 |
| | 100.0 | 100.0 | 99.4 |
| Elsinan | 0 | 0 | 0 |
| | 0.01 | 10.5 | 0 |
| | 0.1 | 27.7 | 21.2 |
| | 0.5 | 83.5 | 81.6 |
| | 1.0 | 91.6 | 87.3 |
| | 5.0 | 96.1 | 93.7 |
| | 10.0 | 97.7 | 96.5 |
| | 100.0 | 98.9 | 98.2 |

As described above, the dry solid of the invention is characterized in that it is freely soluble in water, and that it stably retains the activity of a proteinaceous bioactive substance over a long period of time under vigorous conditions, e.g. at room temperature. Unlike conventional stabilizer such as HSA, the specific polysaccharide has no fear of mediating human infectious diseases, and does not obscure the specific activity of the substance which is used for determination of purification degree.

Thus, the dry solid of the invention is advantageously usable for test reagent, injection, and medicine for internal or external administration, to prevent and/or treat human diseases.

The merits of the present invention will be explained with reference to the following examples.

EXAMPLE 1

HuIFN

A concentrate containing a purified HuIFN, obtained by the method in Experiment 1-A, was added with an aqueous solution containing 100 parts of a purified pullulan based on the weight of HuIFN solid, filtered under sterile conditions, distributed into 2 ml-glass vials to give an HuIFN content of $3 \times 10^6$ U/vial, and freeze-dried.

The product is stable over a long period of time even at room temperature, and readily dissolvable in water. Thus, the product is advantageously usable for test reagent, as well as for intramuscular- or intravenous-injection.

EXAMPLE 2

TNF

A concentrate containing a purified TNF, obtained by the method in Experiment 2-A, was added with an aqueous solution containing 200 parts of a purified pullulan based on the weight of TNF solid, filtered under sterile conditions, distributed into 2 ml-glass vials to give a TNF content of 2,000 U/vial, and freeze-dried.

The product is stable over a long period of time even at room temperature, and readily dissolvable in water. Thus, the product is advantageously usable for test reagent, as well as for intramuscular- or intravenous-injection.

EXAMPLE 3

LT

Non-adsorbed fractions from a column of immobilized anti-HuIFN antibody, obtained by the method in Experiment 1-A, were purified by affinity-chromatography using phytohemagglutinin-Sepharose, and concentrated with a membrane. The concentrate containing a high-purity LT was admixed with an aqueous solution containing 50 parts of elsinan based on the weight of LT solid, distributed into 5 ml-glass vials to give an LT content of 1,000 U/vial, and freeze-dried.

The product is stable over a long period of time even at room temperature, and readily dissolvable in water. Thus, the product is advantageously usable for test reagent, injection, granule, tablet, ointment, etc.

The activity of LT was assayed in conventional manner as reported in *In Vitro Methods in Cell-Mediated Immunity*, edited by B.R. Blood & P.R. Glade, published by Academic Press, Inc. (1971), wherein a culture of mouse L cell is exposed to dilutions of LT, and the number of residual treated L cells is counted.

EXAMPLE 4

GH

An acidophilic adenoma cell was extracted from acidophilic adenoma patient, minced, disaggregated, and subcutaneously implanted into adult nude mice, followed by three week-bleeding. The tumor masses, formed subcutaneously in the animals, about 10 g each, were extracted, minced, and disaggregated in saline containing trypsin. The cell so obtained was washed with glucose-free Earle's 199 medium (pH 7.2) supplemented with 10 v/v % fetal calf serum, suspended in a fresh preparation of the same culture medium, additionally containing 30 mM L-arginine as GH inducer, to give a cell density of about $10^5$ cell/ml, and incubated at 37° C. for six hours to induce hGH production. The cell in the resultant culture was ultrasonically disintegrated, and the hGH in the supernatant was assayed. The hGH production was about 500 ng/ml cell suspension. The supernatant was purified and concentrated in conventional manner to obtain an hGH concentrate which was then admixed with an aqueous solution containing 10,000 parts of pullulan based on the weight of hGH solid, distributed into 2 ml-glass vials to give an hGH content of 10 ng/vial, and freeze-dried.

The product is stable over a long period of time even at room temperature, and readily dissolvable in water. Thus, the product is advantageously usable for test reagent or injection.

The activity of hGH was assayed by conventional radioimmunoassay as described in S.M. Gilick et al., *Nature*, Vol. 199, page 784 (1963).

EXAMPLE 5

EGF

A submaxillary gland tumor cell was extracted from submaxillary gland tumor patient, minced, disaggregated, and inoculated on Earle's 199 medium (pH 7.2), supplemented with 10 v/v % fetal calf serum, to give a cell density of about $1 \times 10^5$ cells/ml. The tumor cell was cultured at 37° C. in a closed system for one week while periodically refreshing the culture medium. When the proliferated cell formed a monolayer, the culture was washed in saline containing a phosphate along with trypsin. The proliferated cell was suspended in a fresh preparation of the same culture medium to give a cell density of about $1 \times 10^5$ cells/ml, and cultured in suspension at 37° C. and pH 7.2 for an additional one week. The cell was then ultrasonically disintegrated, and the hEGF in the supernatant was assayed. The hEGF production was about 1.3 μg/ml cell suspension. After purifying and concentrating the supernatant in conventional manner, the resultant hEGF concentrate was admixed with an aqueous solution containing 200 parts of elsinan based on the weight of hEGF solid, distributed into 5 ml-glass vials to give an hEGF content of 0.5 μg/vial, and freeze-dried.

The product is stable over a long period of time even at room temperature, and readily dissolvable in water. Thus, the product is advantageously usable for test reagent, injection, granule, tablet, suppository, etc.

The activity of hEGF was assayed by conventional radioreceptor assay as described in R.L. Ladda et al., *Analytical Chemistry*, Vol. 93, pp. 286–294 (1979).

EXAMPLE 6

EPO

A human kidney tumor cell was extracted from kidney tumor patient, minced, disaggregated, and suspended in a flask along with Namalwa (a human lymphoblastoid line), with a salt solution, containing 140 mM NaCl, 54 mM KCl, 1 mM $NaH_2PO_4$ and 2 mM $CaCl_2$, to give respective cell density of about $10^3$ cells/ml. The cell suspension was added under ice-chilled conditions with a fresh preparation of the same salt solution but additionally containing Sendai virus preinactivated with uv-irradiation. After a lapse of five minutes, the cell suspension was placed in a 37° C. incubator for about thirty minutes to effect cell fusion. Thus, the hEPO producibility was introduced into the Namalwa cell. Adult nude mice were intraperitoneally implanted with the Namalwa cell, and fed for five weeks in usual way. The tumor masses, formed subcutaneously in the animals, about 15 g each, were extracted, and disaggregated in saline containing trypsin. The cell so obtained was washed with Earle's 199 medium (pH 7.2), supplemented with 10 v/v % fetal calf serum, to give a cell density of about $10^6$ cells/ml, and incubated at 37° C. for twenty hours under a reduced pressure of 700 mmHg to induce hEPO production. The cell was ultrasonically disintegrated, and the hEPO in the supernatant was assayed. The hEPO production was about 170 U/ml cell suspension After purifying and concentrating the supernatant in conventional manner, the resultant hEPO concentrate was admixed with an aqueous solution containing 500 parts of pullulan based on the weight of hEPO solid, distributed into 5 ml-glass vials to give an hEPO content of 10 U/vial, and freeze-dried.

The product is stable over a long period of time even at room temperature, and readily dissolvable in water. Thus, the product is advantageously usable for test reagent or injection.

The activity of hEPO was assayed by conventional bioassay using incorporation of $^{59}Fe$ as reported in P.M. Cotes and D.R. Bangham, *Nature*, No. 4793, pp. 1065–1067 (1961). One Unit (U) of hEPO activity is equal to one-tenth of the hEPO activity in one vial distributed from the WHO.

EXAMPLE 7

TSH

A human basophilic adenoma cell was extracted from basophilic adenoma patient, minced, disaggregated, and suspended along with Namalwa cell in a salt solution, containing 140 mM NaCl, 54 mM KCl, 1 mM NaH$_2$PO$_4$ and 2 mM CaCl$_2$, to give respective cell density of about 10$^4$ cells/ml. The cell suspension was added under ice-chilled conditions with a fresh preparation of the same salt solution but additionally containing Sendai virus preinactivated with uv-irradiation. After a lapse of five minutes, the cell suspension was placed in a 37° C. incubator for about thirty minutes to effect cell fusion. Thus, the hTSH producibility was introduced into the Namalwa cell. Adult nude mice were intraperitoneally implanted with the Namalwa cell, and fed for five weeks in usual way. The tumor masses, formed in the animals, about 15 g each, were extracted, minced, and disaggregated in saline containing trypsin. The cell so obtained was washed with Earle's 199 medium (pH 7.2) supplemented with 10 v/v fetal calf serum, suspended in a fresh preparation of the same culture medium, additionally containing 30 mM L-arginine as TSH inducer, to give a cell density of about 10$^5$ cells/ml, and incubated at 37° C. for thirty-five hours to induce hTSH production. The cell was ultrasonically disintegrated, and the hTSH in the supernatant was assayed. The hTSH production was about 180 mIU/ml cell suspension. After purifying and concentrating the supernatant in conventional manner, the resultant hTSH concentrate was admixed with an aqueous solution containing 100 parts of elsinan based on the weight of hTSH solid, distributed into 5 ml-glass vials to give an hTSH content of 10 mIU/vial, and freeze-dried.

The product is stable over a long period of storage even at room temperature. Thus, the product is advantageously usable for test reagent or injection.

The activity of hTSH was assayed by conventional radioreceptor assay as reported in S.W. Manley et al., *Journal of Endrocrinology*, Vol. 61, pp. 419–436 (1974), and represented by International Unit (IU) with reference to the standard hTSH specimen distributed from the National Institute for Medical Research, England.

While the preferred forms of the present invention have been described, it is to be understood that modifications will be apparent to those skilled in the art without departing from the spirit of the invention. The scope of the invention, therefore, is to be determined solely by the following claims.

We claim:

1. A water-soluble dry solid composition, comprising: one part by weight of a proteinaceous bioactive substance in admixture with at least 0.5 parts by weight of a polysaccharide mainly composed of repeating maltotriose units.

2. The composition in accordance with claim 1, wherein the proteinaceous bioactive substance is a member selected from the group consisting of lymphokine and peptide hormone.

3. The composition in accordance with claim 1, wherein the polysaccharide is a member selected from the group consisting of pullulan, elsinan, their partial hydrolysates, and mixtures thereof.

4. The composition in accordance with claim 1, wherein the molecular weight of the polysaccharide is within the range of 10,000–10,000,000 daltons.

5. The composition in accordance with claim 1, containing between 0.5 and 10,000 parts by weight of said polysaccharide to one part by weight of said proteinaceous bioactive substance.

6. A method for making a water-soluble dry solid composition containing a mixture of one part by weight of a proteinaceous bioactive substance along with at least 0.5 parts by weight of a polysaccharide mainly composed of repeating maltotriose units, said method comprising:
    providing an aqueous solution containing one part by weight of said proteinaceous bioactive substance in admixture with at least 0.5 parts by weight of said polysaccharide; and
    drying the aqueous solution at a temperature below 30° C. and reduced pressure to produce said water-soluble dry solid composition.

7. The method in accordance with claim 6, wherein the proteinaceous bioactive substance is a member selected from the group consisting of lymphokine and peptide hormone.

8. The method in accordance with claim 6, wherein the polysaccharide is a member selected from the group consisting of pullulan, elsinan, their partial hydrolysates, and mixtures thereof.

9. The method in accordance with claim 6, wherein the molecular weight of the polysaccharide is within the range of 10,000–10,000,000 daltons.

10. The method in accordance with claim 6, wherein said drying step is effected by freeze-drying.

11. The method in accordance with claim 6, containing between 0.5 and 10,000 parts by weight of said polysaccharide to one part by weight of said proteinaceous bioactive substance.

* * * * *